United States Patent [19]

Dutchik

[11] Patent Number: 5,590,778
[45] Date of Patent: Jan. 7, 1997

[54] DOUBLE-STERILE PACKAGE FOR MEDICAL APPARATUS AND METHOD OF MAKING

[75] Inventor: Robert A. Dutchik, Laguna Niguel, Calif.

[73] Assignee: Baxter International Inc., Deerfield, Ill.

[21] Appl. No.: 470,851

[22] Filed: Jun. 6, 1995

[51] Int. Cl.⁶ .......................... A61B 17/06; A61B 19/02
[52] U.S. Cl. .......................... 206/439; 206/571; 220/373; 422/34
[58] Field of Search .................................... 206/438, 439, 206/370, 363, 570, 571, 484.1; 220/373, 374; 422/25, 34; 53/425, 426

[56] References Cited

U.S. PATENT DOCUMENTS

| | | |
|---|---|---|
| 2,990,948 | 4/1958 | Zackheim .............................. 206/439 |
| 3,229,813 | 1/1966 | Crowe et al. . |
| 3,410,395 | 11/1968 | Sellers . |
| 3,468,471 | 9/1969 | Linder . |
| 4,022,324 | 5/1977 | Schuster . |
| 4,190,154 | 2/1980 | Clark . |
| 4,482,053 | 11/1984 | Alpern et al. . |
| 4,511,035 | 4/1985 | Alpern .................................. 206/363 |
| 4,689,936 | 9/1987 | Gaikema et al. . |
| 4,754,595 | 7/1988 | Sanderson . |
| 4,863,016 | 9/1989 | Fong et al. . |
| 4,884,694 | 12/1989 | Sengewald . |
| 4,971,196 | 11/1990 | Kitamura et al. . |
| 5,014,493 | 5/1991 | West . |
| 5,277,741 | 1/1994 | Kramer . |
| 5,322,161 | 7/1994 | Shichman et al. . |
| 5,344,017 | 6/1994 | Wittrock . |

FOREIGN PATENT DOCUMENTS

| | | |
|---|---|---|
| 142378 | 11/1984 | European Pat. Off. . |
| 269410 | 11/1987 | European Pat. Off. . |
| 352708 | 7/1989 | European Pat. Off. . |
| 2240483 | 8/1972 | Germany . |
| 3455645 | 12/1985 | Germany . |
| 4200266 | 1/1992 | Germany . |
| 7412980 | 4/1976 | Netherlands . |
| 1488326 | 1/1976 | United Kingdom . |
| WO91/11374 | 8/1991 | WIPO . |

OTHER PUBLICATIONS

MULTIVAC advertisement, Medical Device and Diagnostic Industry, Feb. 1995.

Primary Examiner—Bryon P. Gehman
Assistant Examiner—N. Shian Lam
Attorney, Agent, or Firm—Poms Smith Lande & Rose; Bruce Canter

[57] ABSTRACT

A double-sterile package for critical-use medical apparatus includes an inner first container including an outer boundary wall impervious to microorganisms and being closed except for defining a hole. A patch of gas-permeable micro-porous sheet material is secured to the outer boundary wall spanning and closing the hole. The gas-permeable sheet material is sufficient to exclude environmental microorganisms from entering the inner first container. The first container is received into and nested within a conformal second container also having a boundary wall impervious to microorganisms and being closed except for defining a hole. This hole of the second container is also closed by a patch of the gas-permeable micro-porous sheet material, and the holes of the first and second containers are in gas-flow communication with one another. The medical apparatus within the nested containers is sterilized by evacuation of air and introduction of a sterilizing gas via the gas-permeable patches. Removal of the sterilizing gas provides a packaged sterile medical apparatus which may be transported, stored, and handled with no further need to additionally protect the sterility of the apparatus, or for further sterilization after the package is opened immediately prior to use of the apparatus.

12 Claims, 3 Drawing Sheets

DOUBLE-STERILE PACKAGE FOR MEDICAL APPARATUS AND METHOD OF MAKING

BACKGROUND OF THE INVENTION

1. Field of the Invention

The present invention is in the field of sterile packaging for medical apparatus, and method for making such packaging. More particularly, the present invention relates to so called double-sterile packaging for medical apparatus. With this packaging, a newly manufactured non-sterile medical apparatus, such as a cardiac catheter, is first enclosed in an inner first container sufficient to isolate the apparatus from microorganisms in the environment. This inner first container is itself packaged in an outer second container which is also sufficient to isolate the inner first container and apparatus from microorganisms in the environment. The first and second containers each include cooperative areas of a micro-porous sheet material which will freely pass gas molecules, but which will not pass microorganisms from the environment into the containers.

These nested containers are processed in a chamber to remove air from within the containers via the micro-porous sheet material, and to replace the air with a sterilizing gas, such as ethylene oxide. After an interval of time sufficient to insure that all microorganisms inside both the inner and outer containers have been killed, the sterilizing gas is removed and replaced with an inert gas. Subsequently, the packaged medical apparatus is shipped to a site of future use, and may be stored in its double-sterile package on a shelf open to the ambient air, for example, without further need for protection from microbes until the time of its use arrives. When the time arrives to use the packaged apparatus, it may be removed from the double-sterile package and used for human treatment without any need for further sterilization immediately prior to this time of use.

2. Discussion of the Related Technology

Conventional packaging for medical apparatus includes single-sterile packages, one embodiment of which is the familiar envelope found on adhesive bandages, such as on a Band-aid. Another embodiment of such single-sterile packaging takes the form of essentially a plastic bag made of a heat-sealable plastic sheet material. A medical apparatus may be placed into such a bag and the opening of the bag is then heat sealed shut. In order to allow sterilization of the packaged medical apparatus, the bag includes a hole in at least one wall. This hole is spanned and closed by a patch of gas-permeable material which will pass sterilizing gas but not microorganisms. As described above, the packaged medical apparatus is sterilized by use of a processing chamber and a sterilizing gas, such as ethylene oxide.

In such single-sterile packages, the gas-permeable patch may be made of a spun polyolefin sheet material. This material has an appearance, consistency, and feel generally like heavy bond paper, but is considerably stronger than an equivalent weight of paper because it is spun or matted of polyolefin fibers rather than from cellulose (wood fibers) or from other organic fibers (such as rag or cotton). An example of such sheet polyolefin material is available commercially under the trade name of TYVEK from Dupont Company. This TYVEK sheet material is micro-porous so that a sterilizing gas may pass readily therethrough. However, TYVEK sheet material will not pass microorganisms from one side to the other because the porosities of the material are simply too small. In order to secure the patch of TYVEK material to the wall of the heat-sealable bag, a peripheral annular part of the patch is heat sealed to the sheet plastic material from which the bag wall is formed. In this case, because the bag is polyethylene sheet material and the TYVEK patch is essentially polyethylene material, these two materials are essentially common to one anther, and can be heat sealed together.

Such single-sterile packaging bags are generally used for storing medical devices which are not of a critical nature. However, for storing critical medical devices (such as cardiac catheters and other apparatus which are either to be used with critical patients, or which are to be introduced deeply into the human body, or both), so that the risk of serious and possibly fatal infection from a lack of absolute sterility is great, then a higher level of protection for the sterility of the apparatus is required of the packaging used for this apparatus. For these critical-use medical apparatus, a double-sterile package technology has been developed.

A conventional double-sterile package for a cardiac catheter includes an inner first container having a tray-like member formed of substantially rigid and shape-retaining plastic sheet material. This tray-like member defines a recess or recesses into which the components of the cardiac catheter are received, and also defines an upper out-turned planar peripheral flange which completely circumscribes and defines an opening to the recess of the tray-like member. In order to close this opening defined within the peripheral flange, a single continuous flat closure sheet of micro-porous material spans across and closes this opening. This closure sheet may be made of TYVEK sheet material, for example. The closure sheet of micro-porous material rests upon and heat-seal bonds to the out-turned flange of the tray-like member continuously around the periphery of the recess in this member.

A heat-seal bond is defined between the flange feature of the tray-like member and the flat closure sheet of micro-porous material. This sheet of micro-porous material alone would not heat seal bond to the plastic material from which the tray-like member is formed. In order to effect this heat-seal bond, the sheet of micro-porous material carries on its inner face a dispersed or discontinuous layer of heat-bonding material. This layer of heat-bonding material must be dispersed or discontinuous in order to preserve some of the porosity of the micro-porous sheet material. This heat-bonding material is effective upon the application of localized pressure and elevated temperature, as in a heat-sealing machine, to effect the necessary heat-seal bond between the closure sheet and tray-like member. This heat-seal bond is circumferentially continuous and is impervious to microorganisms in the environment, but may be peeled open by manual force.

The inner first container is received into an outer second container, which is essentially a partially transparent plastic bag. The outer second container has a pair of generally unequally-sized rectangular flat opposed walls, one made entirely of flexible transparent plastic sheet material, and the other being made partly of flat transparent plastic sheet material, and partly of flat micro-porous sheet material. These two flat walls are heat sealed to one another along three edges to form a rectangular bag with one open edge. The one wall of flexible plastic sheet material extends beyond the portion of the opposite wall which is formed by such plastic sheet material. This extension of the longer wall is confronted by a closure flap portion of the opposite wall which is formed by the micro-porous sheet material. This closure flap portion is also coated on its inner face with heat-bond material, as is described above.

In the manufacture of this outer container bag, the shorter wall is formed with the closure flap heat sealed along one edge of the shorter wall leaving an extending free-flap part of the closure flap overlying the shorter wall. This free-flap portion provides for later manual grasping of the flap so that the outer container bag can be peeled open. The closure flap is sized so that it makes up the difference in size between the two walls of plastic sheet material, and is congruent at its marginal edge with the marginal edge of the longer wall. Thus, the longer wall of plastic sheet material and the closure flap of micro-porous sheet material leave an open edge to the bag through which the inner container may be inserted. After the inner container is inserted into the outer container bag, the open edge of the outer container bag is heat sealed closed. That is, the longer wall of plastic sheet material and the closure flap of micro-porous sheet material are heat-seal bonded to one another at their congruent marginal edge portions. A continuous heat-seal closure is thus formed for the outer container bag. This double-sterile package is then inserted into a handling and storage box. Although this box is primarily for handling and storage purposes, it additionally provides a convenient space upon which important information about the medical apparatus can be printed in a number of languages. A number of such boxed and packaged medical apparatus are sterilized simultaneously using a sterilizing gas, as is described.

More particularly, the contents of this conventional double-sterile package within its handling and storage box are sterilized in the conventional way using a sterilizing gas, such as ethylene oxide. Adequate ventilation of the sterilizing gas both into and out of the recesses of the inner first container, and to and from the surfaces of the cardiac catheter therein, is provided because the closure flap of the outer container bag overlays a portion of the closure sheet of the inner container. Some additional ventilation of the inner first container may be achieved via the remainder of the micro-porous closure sheet, even though this remainder portion is overlaid or covered by the impermeable plastic sheet material of the outer container bag.

With a conventional double-sterile package for medical apparatus as described above, the micro-porous closure sheet of the inner first container and the micro-porous sheet material closure flap of the outer container bag each carry a dispersed or discontinuous layer of heat-sealing material on their inner surfaces. This layer of heat-sealing material reduces the permeability of the micro-porous sheet material by a factor of about 10. That is, the permeability of the micro-porous sheet material is reduced from its value of about 20 seconds per 100 cc per square inch (hereinafter sec/100 cc/sq.in.) in its un-coated state to about 150–200 sec/100 cc/sq.in., with the layer of heat-sealing material. As a result, in order to achieve adequate ventilation of the sterilizing gas to and from the surfaces of the packaged medical apparatus, a considerable area of the micro-porous sheet material must be used in each conventional double-sterile package. This ventilation rate for a package is a function of contained volume within the package and the permeability of the micro-porous sheet material. If this ventilation rate is not maintained for a particular package design, then the time required for the sterilizing operation is considerably increased, adding significantly to the costs of the medical apparatus as delivered to a patient. However, the micro-porous sheet material is itself very expensive, and the relatively large amount of this material used in each conventional double-sterile package for a medical device adds significantly to the costs of these devices.

Additionally, the conventional double-sterile package as described above has a number of deficiencies. Because of the nature of the outer container bag, this bag has only a limited amount of space upon which important information about the medical device and its use can be printed. This limited space is defined substantially only on the closure flap of micro-porous sheet material. This closure flap conventionally represents only about one-third or less of the area of one side of the outer container bag. This important information about the medical apparatus must additionally be provided in a number of languages because of the international use of many medical apparatus. Consequently, this lack of available informational space on the outer surfaces of the outer container bag of a conventional double-sterile package is another reason for use of the outer handling and storage box. The important information about the medical apparatus is printed on the outer surface of the box. However, because the handling and storage box is frequently opened first and discarded, while preparations are under way for use of the medical apparatus, information which is set out on the box must be repeated on the double-sterile package itself. As a result, the surface of both the closure flap of the outer container bag, and of the closure sheet of the inner container (which is visible even while the outer container bag is closed because this bag is formed mostly of transparent plastic sheet material) are additionally printed with this important information. Thus, the conventional packaging requires duplicated printing operations because the box is frequently thrown away at an early time.

Further to the above, when a medical apparatus in a conventional boxed double-sterile package is to be used, medical personnel must first open the box and remove the double-sterile package. The outer container bag of the double sterile package is opened next by peeling open the closure flap of the outer container bag. This allows removal of the inner container from the outer container bag. The inner first container is then opened as a third step by peeling open the closure sheet from the tray-like member. Thus, a three-step opening procedure is required under conditions which are frequently rushed and exigent. Additionally, all of the packaging material for the medical apparatus, including the outer handling and storage box, must ordinarily be treated as contaminated biological waste, which requires expensive special protective disposal procedures.

Further the conventional double-sterile package includes an outer bag-like container, as has been described. This outer container bag is generally rectangular in plan shape. Because the inner container is not necessarily rectangular in plan shape, the two containers define therebetween corner areas outside of the inner container but within the outer container. These corner area define interstitial pocketed or stagnant volumes within which sterilizing gas may accumulate during the sterilizing process, and from which this gas must be purged before the process is considered complete. These interstitial pocketed volumes are not necessary because no part of the packaged medical apparatus is contained outside of the inner container. However, the inner surface of the outer package and the outer surface of the inner package must both be sterile. Thus, there is a real need to ventilate sterilizing gas to and from these pocketed volumes. Because the common sterilizing gasses, such as ethylene oxide, are known or suspected to be powerful carcinogens, considerations of long term exposure for medical personnel who are involved in opening such packages prior to use of the medical apparatus therein dictates that all sterilizing gas be purged from the package. Consequently, such double-sterile packages which define stagnant volumes or pockets such as at the corners of the conventional outer container bag, may require longer sterilizing and purging processes than would otherwise be necessary. Minimizing these stagnant volumes between the inner and outer package is important because their presence increases gas sterilizing processing times and decreases package throughput at the sterilizing facility. Thus, such longer processing times for the sterilizing process significantly increases the cost for the medical apparatus.

SUMMARY OF THE INVENTION

In view of the deficiencies of the conventional technology, an object for this invention is to provide a double-sterile packaging for medical apparatus which avoids one or more of these deficiencies.

Another object for this invention is to reduce the requirements for use of micro-porous sheet material in a double-sterile package for medical apparatus.

Yet another object for this invention is to provide a double-sterile package for medical apparatus which reduces the amount of total packaging materials used, which packaging materials must be considered as actual or potential biological waste after their use.

Still another object for this invention is to provide a double-sterile package for medical apparatus which virtually eliminates interstitial stagnant or pocketed volumes within the packaging so that processing time to sterilize the contents of the package is not adversely affected by the presence of such volumes.

Accordingly, the present invention provides a double-sterile package comprising: an inner shape-retaining container including a boundary wall impervious to microorganisms and being closed except for defining a hole, the boundary wall bounding a volume for receiving an article; a patch of gas-permeable micro-porous sheet material sealingly secured to the boundary wall of the inner container, the patch spanning and closing the hole in the inner container boundary wall and being sufficient to exclude environmental microorganisms from entering the inner container; a conformal shape-retaining outer container receiving and nesting with the inner container, the outer container also having a boundary wall impervious to microorganisms and being closed except for defining a respective hole; a patch of gas-permeable micro-porous sheet material sealingly spanning and closing the hole of the outer container, the patch of micro-porous sheet material of the outer container also being sufficient to exclude environmental microorganisms from entering the outer container; the holes of the first and second containers being in gas-flow communication with one another; whereby a sterilizing gas may be introduced into the volume via the holes and the gas flow communication therebetween through the gas-permeable patches of the inner and outer containers to sterilize the article, and environmental microorganisms being thereafter excluded from the article by the micro-porous patches to maintain sterility of the article.

According to another aspect, the present invention provides a method of making a double-sterile package, the method comprising steps of: providing an inner container having a boundary wall impervious to microorganisms and being closed except for defining a hole; using the boundary wall of the inner container to define a volume for receiving an article; providing a patch of gas-permeable micro-porous sheet material; sealingly securing the patch of gas-permeable micro-porous material to the boundary wall of the inner container to span and close the hole in the inner container boundary wall; insuring that the patch of gas-permeable micro-porous material is sufficient to exclude environmental microorganisms from entering the inner container via the hole; providing an outer container receiving and nesting with the inner container, providing the outer container also with a respective boundary wall impervious to microorganisms and being closed except for defining a respective hole; providing a respective patch of gas-permeable micro-porous sheet material; sealingly securing the respective patch of gas-permeable micro-porous sheet material to the boundary wall of the outer container to span and close the respective hole of the outer container; insuring that the patch of micro-porous sheet material of the outer container is also sufficient to exclude environmental microorganisms from entering the outer container; providing gas flow communication between the holes of the first and second containers; introducing a sterilizing gas into the volume via the holes and the gas flow communication therebetween through the gas-permeable patches of the inner and outer containers to sterilize the article; and thereafter using the micro-porous patches to exclude environmental microorganisms from the article to maintain sterility of the article.

Some salient advantages resulting from the present invention are the reduction in use of micro-porous sheet material by a factor of about 10, the reduction of the amount of packaging material by the elimination for the need of an outer handling and storage box, and the virtual elimination of interstitial pocketed volumes within the package.

These and other additional objects and advantages of the present invention will appear from a reading of the following description of a particularly preferred exemplary embodiment of the invention taken in conjunction with the appended drawing Figures, in which the same reference numeral refers to features of the several Figures which are the same or which are analogous to one another in structure or function.

DESCRIPTION OF THE DRAWING FIGURES

FIG. 1 provides a top perspective view of a double-sterile package for a medical apparatus;

Figure 1:
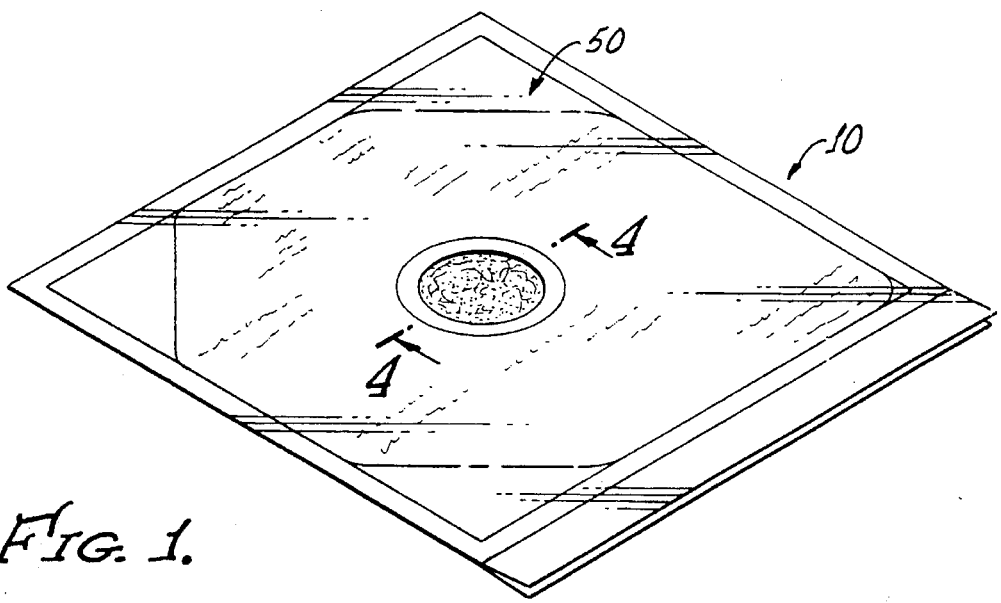
Figure 4:
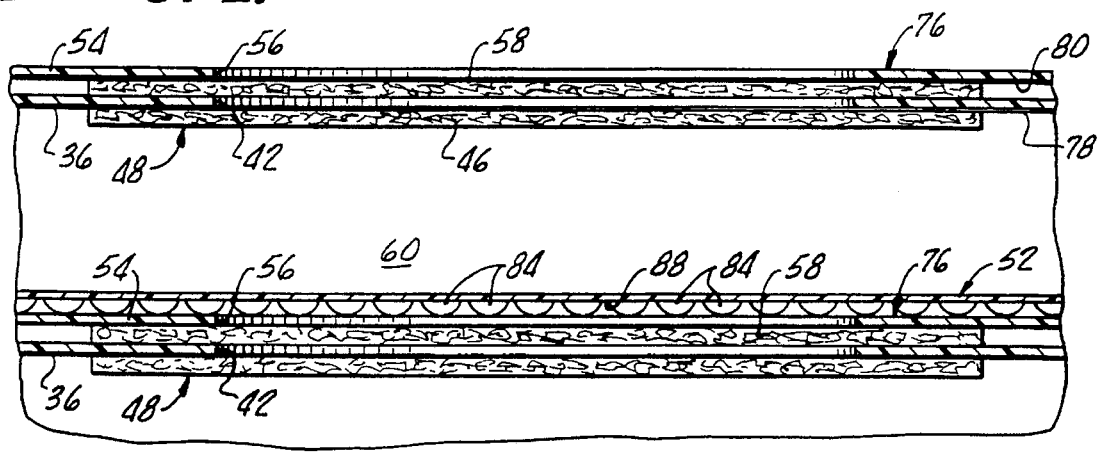
Figure 5:
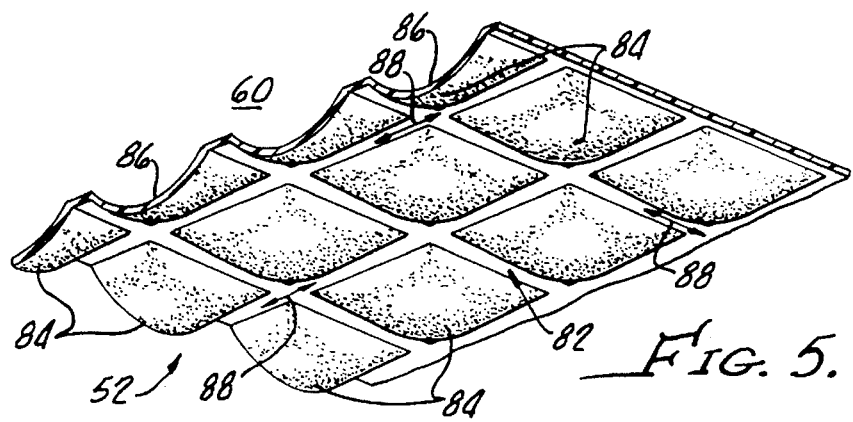
Figure 6:
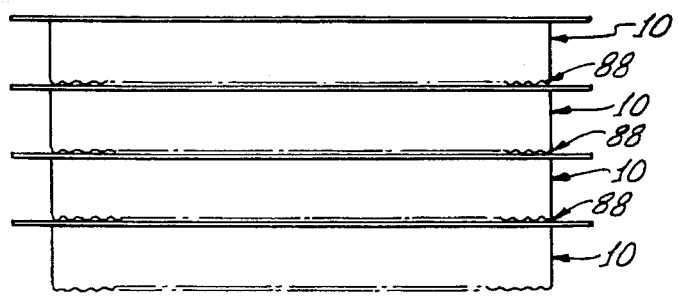

FIG. 4 provides a greatly enlarged and somewhat schematic fragmentary cross sectional view taken generally at plane 4—4 of FIG. 1;

FIG. 5 depicts a greatly enlarged fragmentary perspective view of a portion of the bottom of the double-sterile package, particularly as it would appear when viewed from below; and FIG. 6 provides a side elevation view of several of the packages seen in the preceding Figures, as they are stacked for sterilizing of the contents of these packages.

DETAILED DESCRIPTION OF AN EXEMPLARY PREFERRED EMBODIMENT

Figure 2:
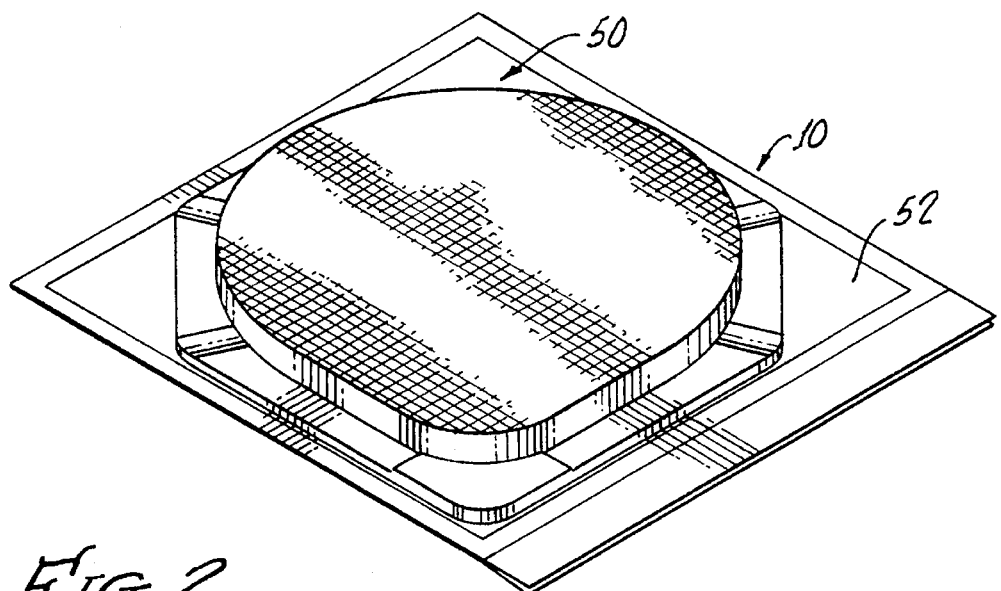
FIG. 2 is a bottom perspective view of the double-sterile package seen in FIG. 1.
Figure 3:
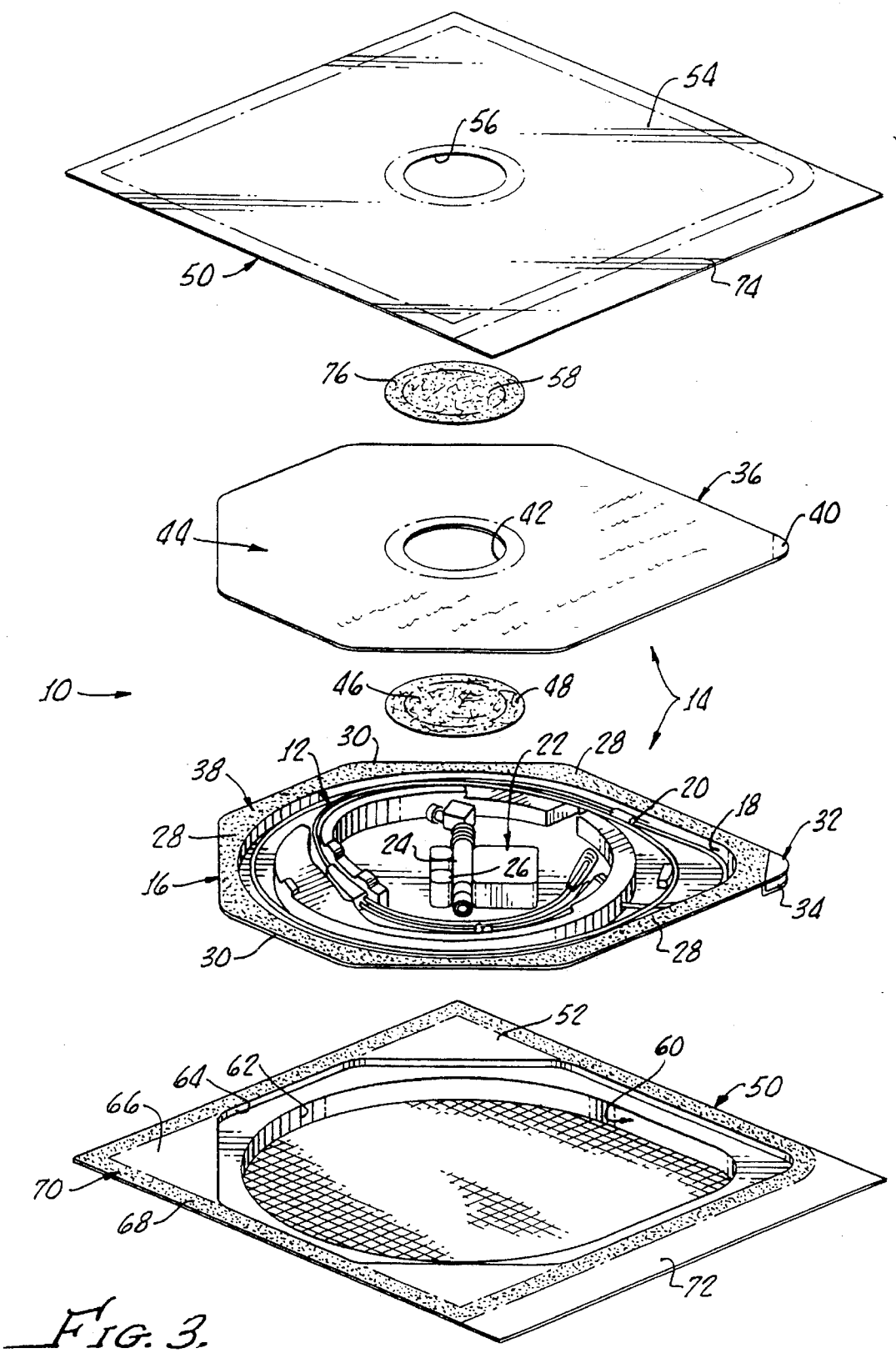
FIG. 3 is an exploded perspective view of the double-sterile package seen in FIGS. 1 and 2, with parts of this package separated for clarity of illustration.

Considering first FIGS. 1, 2, and 3 in conjunction with one another, a double-sterile package 10 for containing a medical apparatus 12 (seen in FIG. 3) is depicted. The double sterile package 10 includes an inner first container 14, seen in its component parts in FIG. 3. The inner first container 14 includes a generally rigid and shape-retaining tray-like member 16, which may preferably be vacuum formed of plastic sheet material. Because the tray-like member is vacuum formed of sheet plastic material, its outer configuration is a complement of its inner configuration. The tray-like member 16 defines a configured and generally spiral recess 18, within which the medical apparatus 12 is received. The medical apparatus 12 in this instance is an elongate flexible cardiac catheter, referenced particularly with the numeral 20. The elongate catheter 20 is spirally wrapped into the recess 18. In a central portion 22 of the recess 18, a syringe 24 is disposed in a shape-matching recess 26. This syringe 24 is for use in purging the catheter 20 prior to use. However, it will be understood that other configurations may be selected for the package 10 in order to package other medical apparatus 12 with double-sterile packaging.

Circumscribing the recess 18, the tray-like member 16 includes an outwardly extending and circumferentially continuous planar flange portion 28. The flange portion 28 is at an elevation above all of the recess 18, and above the upper level of all parts of the medial apparatus 12 placed into this recess. An outer peripheral edge surface 30 of the flange 28 defines a polygonal shape, which can be seen generally in plan view in FIG. 2. This polygonal shape of the outer edge surface 30 of flange 28 may be seen generally to have 7 sides, and 7 vertices or corners. One of the corners, indicated with the numeral 32, extends outwardly further than the other six corners, subtends an angle of substantially 90 degrees, and terminates in a portion 34 which is offset downwardly out of the plane of the flange 28, for a purpose to be described.

Sealingly received upon the flange 28 is an opaque closure sheet 36 of plastic material. This closure sheet 36 in plan view has a size and shape matching that of the outer periphery (i.e., at surface 30) of flange 28. The sheet 36 of plastic material is heat sealed to the flange 28 in an area indicated with the stippling 38 on this flange in FIG. 3. As will be further explained, the closure sheet on its surface confronting the tray-like member 16 carries a coating of material for heat sealing. The heat seal so formed between closure sheet 36 and the tray-like member 28 is impermeable to microorganisms, and has good tenacity. However, this heat seal 38 may be peeled open with manual force. As is seen in FIG. 3, the heat seal area 38 extends diagonally across a portion of flange 28 at corner 32 which is spaced slightly inwardly of the offset in member 28 for portion 34. As a result, a free tab portion of closure sheet 36, indicated with the numeral 40, is not bonded to the underlying flange 28, and is available to be manually grasp in opposition to the portion 34 in order to peel open the inner first container 14.

Viewing the closure sheet 36 more particularly, it is seen that this sheet includes a central hole 42. Closure sheet 36 also provides a considerable facial area, indicated generally with the arrow 44, upon which informational printing is provided, preferably in a number of languages. Because the closure sheet 36 is opaque, and is preferably white in color, the printing on this sheet is easily read.

Inner first container 14 also includes a patch 46 or disk of micro-porous sheet material, which is heat sealed to the closure sheet in a circumferentially continuous annular peripheral area of this patch, indicated with the stippling and numeral 48 on FIG. 3. The patch 46 spans and closes the hole 42. Patch 46 is made of un-coated micro-porous sheet material, and has the corresponding permeability rate of about 20 sec/100 cc./sq.in. Preferably, the patch 46 may be formed of TYVEK sheet material. As mentioned above, the closure sheet 36 carries on its inner surface (facing the tray-like member 16) a layer or coating of heat-seal material, which is further described below. Consequently, as will be further explained, the patch 46 is heat sealed to the closure sheet 36 by use of this heat-seal layer on the sheet 36 itself. The patch 46 does not carry any material which would facilitate its heat sealing to another plastic substrate, and would not so bond to the sheet 36 except for the layer of heat-seal material on this sheet.

Outer container 50 is transparent on its top side, and includes a flexible, yet shape-retaining, conformal outer tray-like member 52, a flat transparent closure sheet 54 defining a central hole 56, and a patch or disk of microporous sheet material 58. Considering first the outer tray-like member 52, it is seen that this tray-like member defines a stepped recess 60. A deeper portion 62 of the recess 60 has a generalized shape and size conformal to the recess 18, recalling that the tray-like member 16 protrudes on its lower side in the complement of this recess. A shallower portion 64 of the recess 60 is conformal to the size and shape of the flange portion 28 of the tray-like member 28 at its outer edge surface 30. An outwardly extending flange portion 66 of the outer tray-like member 52 defines an outer peripheral edge surface 68 which is rectangular in plan view.

Closure sheet 54 heat seals to the flange portion 66 of outer tray member 52 in a circumferentially continuous area indicated with the stippling and numeral 70 on FIG. 3. This heat-seal area is spaced inwardly from an outwardly extending portion 72 of the flange 66, and from an end portion 74 of closure sheet 54. Consequently, the portions 72 and 74 are available to be manually grasp in opposition in order to peel open the outer container 50. The heat seal effected between tray 52 and closure sheet 54 is circumferentially continuous and impermeable to microorganisms, but is of such a strength that it may be manually peeled open.

Heat sealed over the hole 56 is patch 58 of micro-porous sheet material. As was pointed out above with respect to the patch 46 heat sealed at hole 42, the patch 58 is secured to the closure sheet 54 at a circumferentially continuous annular peripheral area indicated with the stippling and numeral 76 on FIG. 3. It will be noted that the holes 42, 56, and patches 46, 58 are congruent when the inner container 14 is received into the outer container 50. Further, the conformal nature of the outer container 50 to the inner container 14 insures that this relationship of congruence (and therefore of gas flow communication) between the holes 42, 56, and patches 46, 58, can not be lost by relative movement between the containers 14 and 50.

Turning attention now to FIG. 4, a greatly enlarged and somewhat diagrammatic cross sectional view is provided taken at line 4—4 of FIG. 1. This enlarged cross sectional view depicts the overlaying closure sheet 54 with hole 56 in congruence with hole 42 of closure sheet 36. The two patches 46, and 58 of micro-porous sheet material span and close these respective holes. The closure sheets 36 and 54 each include a respective inner layer of heat-seal material 78 and 80. These layers of heat-seal material are continuous over the inner surfaces of the sheets 36, and 54, and are used to effect the heat seals of these sheets to the respective tray-like members 16 and 52 (i.e., at areas 38 and 70). The layers 78 and 80 of heat-seal material also effect the heat-seal bonds to patches 46 and 58 at areas 48 and 76. Without the layers 78 and 80 of heat-seal material, the closure sheets 36 and 54 would not heat seal to the patches 46 and 58 of micro-porous material. That is, the patches 46 and 58 are made of sheet micro-porous material which does not have a layer of heat-seal material applied to one side thereof, in contrast to the micro-porous sheet material used in the conventional double-sterile package described above. The sheets 36 and 54 are materially incompatible with the patches 46 and 58 for purposes of heat seal bonding. On the other hand, because the heat-seal material is carried on the closure sheets 36 and 54, the patches 46 and 58 can be bonded thereto using a conventional heat-seal process and still retain their full permeability rating of about 20 sec/100 cc/sq.in.

FIG. 5 provides a greatly enlarged perspective view partially in cross section of a portion of the bottom wall of the outer tray member 52, generally as this tray member wall would appear if viewed from below. As is seen in FIG. 5, the bottom surface is composed of a multitude of small spaced apart bumps 84, each formed by a corresponding dimple on the inside of the plastic sheet material forming this tray member (i.e., in the deeper portion 62 of the recess 60). Because of the bumps 84, the bottom surface 82 of the outer tray-like member 52 defines a plurality of gas flow channels, indicated with the arrows 88 on FIG. 5.

FIG. 6 shows that two or more of the double-sterile packages 10 may be stacked one atop the other for purposes of carrying out the gas-sterilizing described above. Under these circumstances, the channels 88 insure that gas flow ventilation is provided to the holes 42 and 56, and micro-porous patches 46 and 58 of the underlying packages 10. Consequently, all of the medical devices in the stacked packages are assured of receiving full and effective gas sterilization during the process as described. These passages 88 also ensure that purging ventilation is effective for all of the underlying ones of the stacked packages 10, so that no residue of the sterilizing gas is retained in any of the stacked packages 10 after the process. This aspect of full flow of both sterilizing gas and purging gas to and from the underlying packages 10 is especially important because moisture elicited from the packages during this process, which employs the repeated application of a vacuum, may otherwise cause the sheets of plastic material from which the packages are formed to stick together and form an effective gas seal. The pattern of bumps and passages on the lower surface of the packages 10 prevents any underlying package from being prevented form receiving full sterilizing and purging gas flow.

An important advantage of the present invention is that the closure sheet 36 provides adequate area upon which informational printing may be set out. Consequently, no handling and storage box is needed or is used with the package 10. A considerable reduction in biological waste results from the present invention over the conventional double-sterile packages. Additionally, the area of the patches 46 and 58 is only about one-tenth or less of the area of micro-porous sheet material required by the conventional double-sterile packages. Consequently, because this micro-porous sheet material is so expensive, a considerable reduction in cost is offered by the present invention. Despite this reduction by a factor of about 10 in the use of the micro-porous sheet material, the present double-sterile package achieves an equivalent ventilation factor because the micro-porous sheet material used for this package is without the conventional layer of heat-sealing material. This un-coated sheet micro-porous material has a compensating increase in permeability of about 10 over the conventional coated sheet material. Because the patches 46 and 58 are relatively small in size, while the cover sheet 36 provides adequate area for printing and cover sheet 54 is transparent, no printing need be applied to the patches 46 or 58 of micro-porous material. There are virtually no interstitial stagnant or pocketed volumes in the present container. Ventilation of the sterilizing gas to and from the packaged medical apparatus takes place via the directly communicating patches of micro-porous material. Purging of this sterilizing gas is also similarly expedited because of the direct communication via the congruent patches of micro-porous material outwardly from the volume of the package to the surrounding ambient.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope Of the invention. Consequently, the invention is intended to be limited only by the spirit and scope of the appended claims, giving full cognizance to equivalents in all respects.

I claim:

1. A double-sterile package comprising:

an inner shape-retaining container including a boundary wall impervious to microorganisms and being closed except for defining a hole, said boundary wall bounding a package volume for receiving an article;

a patch of gas-permeable micro-porous sheet material sealingly secured to said boundary wall of said inner container, said patch spanning and closing said hole in said inner container boundary wall and being sufficient to exclude environmental microorganisms from entering said inner container;

a conformal shape-retaining outer container receiving and nesting with said inner container, said outer container also having a boundary wall impervious to microorganisms and being closed except for defining a respective hole;

a patch of gas-permeable micro-porous sheet material sealingly spanning and closing said hole of said outer container, said patch of micro-porous sheet material of said outer container also being sufficient to exclude environmental microorganisms from entering said outer container;

said holes of said first and second containers being in gas-flow communication with one another;

whereby a sterilizing gas may be introduced into said package volume via said holes and the gas flow communication therebetween through said gas-permeable patches of said inner and outer containers to sterilize said article, environmental microorganisms being excluded from said article after this sterilizing by said micro-porous patches to maintain sterility of said article.

2. The double-sterile package of claim 1 wherein said patch of gas-permeable micro-porous sheet material which is sealingly secured to said boundary wall of said inner container is free of heat sealing material and provides a permeability of substantially 20 seconds per 100 cubic centimeters per square inch.

3. The double-sterile package of claim 1 wherein said patch of gas-permeable micro-porous sheet material which is sealingly spanning and closing said hole of said outer container is free of heat sealing material and provides a permeability of substantially 20 seconds per 100 cubic centimeters per square inch.

4. The double-sterile package of claim 1 wherein said inner shape-retaining container includes a substantially rigid and shape-retaining tray-like member defining a recess therein, and a closure sheet spanning and closing said recess except for said hole which is defined by said closure sheet, said closure sheet and said tray-like member in said recess thereof cooperatively defining said package volume for receiving an article.

5. The double-sterile package of claim 4 wherein said substantially rigid and shape-retaining tray-like member of said inner shape-retaining container includes an outwardly extending planar flange portion circumscribing said recess, and said closure sheet sealingly engaging said flange portion to span and close said recess.

6. The double-sterile package of claim 4 wherein said closure sheet is impermeable except for said hole, and said closure sheet providing an area upon which printed matter is carried.

7. The double-sterile package of claim 1 wherein said conformal shape-retaining outer container includes a flexibly shape-retaining outer tray-like member receiving and nesting with said inner container.

8. The double-sterile package of claim 7 wherein said inner shape-retaining container includes a substantially rigid and shape-retaining tray-like member defining a recess therein, said tray-like member of said inner container defining an outwardly extending planar flange portion circumscribing said recess, and said closure sheet sealingly engaging said flange portion to span and close said recess, said flexibly shape-retaining outer tray-like member of said conformal shape-retaining outer container defining a stepped recess, a deeper recess portion of said stepped recess receiving a protruding portion of said inner substantially rigid and shape-retaining tray-like member, which protruding portion is complementary to said recess, and a shallower portion of said stepped recess receiving and nesting with said outwardly extending planar flange portion of said inner tray-like member.

9. The double-sterile package of claim 8 wherein said patch of gas-permeable micro-porous sheet material which is sealingly secured to said boundary wall of said inner container is congruent with said patch of gas-permeable micro-porous sheet material which is sealingly spanning and closing said hole of said outer container.

10. The double-sterile package of claim 8 wherein said flexibly shape-retaining outer tray-like member of said conformal shape-retaining outer container includes a lower wall portion downwardly closing said stepped recess, said lower wall portion of said conformal shape-retaining outer container including a plurality of downwardly extending protrusions cooperatively defining a fluid flow channel, whereby when two of said double-sterile packages are stacked one atop the other the package volume of the underlying one of said containers is ventilated via said channel.

11. The double-sterile package of claim 1 wherein said conformal shape-retaining outer container is sufficiently conformal with said inner container that no significant interstitial pocketed volume is defined within said outer container and outside of said inner container, whereby ventilation of gas to and from said package volume occurs via said gas flow communication between said holes but significant gas flow communication interstitially of said first and second containers is avoided.

12. A method of making a double-sterile package, said method comprising steps of:

providing an inner container having a boundary wall impervious to microorganisms and being closed except for defining a hole;

using said boundary wall of said inner container to define a volume for receiving an article;

providing a patch of gas-permeable micro-porous sheet material;

sealingly securing said patch of gas-permeable micro-porous material to said boundary wall of said inner container to span and close said hole in said inner container boundary wall;

insuring that said patch of gas-permeable micro-porous material is sufficient to exclude environmental microorganisms from entering said inner container via said hole;

providing an outer container receiving and nesting with said inner container, providing said outer container also with a respective boundary wall impervious to microorganisms and being closed except for defining a respective hole;

providing a respective patch of gas-permeable micro-porous sheet material;

sealingly securing said respective patch of gas-permeable micro-porous sheet material to said boundary wall of said outer container to span and close said respective hole of said outer container;

insuring that said patch of micro-porous sheet material of said outer container is also sufficient to exclude environmental microorganisms from entering said outer container;

providing gas flow communication between said holes of said first and second containers;

introducing a sterilizing gas into said volume via said holes and the gas flow communication therebetween through said gas-permeable patches of said inner and outer containers to sterilize said article; and thereafter using said micro-porous patches to exclude environmental microorganisms from said article to maintain sterility of said article.

* * * * *